United States Patent [19]

Powers

[11] Patent Number: 4,534,357

[45] Date of Patent: Aug. 13, 1985

[54] MULTIPLE DEMODULATION FREQUENCY DOPPLER

[75] Inventor: Jeffry E. Powers, Bainbridge Island, Wash.

[73] Assignee: Advanced Technology Laboratories, Inc., Bellevue, Wash.

[21] Appl. No.: 601,815

[22] Filed: Apr. 19, 1984

[51] Int. Cl.$^3$ .............................................. A61B 10/00
[52] U.S. Cl. ................................... 128/663; 73/861.25
[58] Field of Search ................... 128/663; 367/90, 94; 343/402, 405, 418; 73/861.25, 602, 620

[56] References Cited

U.S. PATENT DOCUMENTS 3,302,161  1/1967  Ellison .................................... 367/90
3,987,673  10/1976  Hansen ................................ 128/663
4,453,165  6/1984  Maine .................................... 343/418

Primary Examiner—Kyle L. Howell
Assistant Examiner—Ruth S. Smith
Attorney, Agent, or Firm—Lawrence S. Levinson; Sanford J. Asman

[57] ABSTRACT

The device uses two Doppler receivers having different center frequencies. After the mean Doppler frequency of each receiver is determined, one of the mean Doppler frequencies is subtracted from the other one of the mean Doppler frequencies, thereby providing the mean Doppler frequency associated with a frequency which is equal to the difference between the two original frequencies. As this difference frequency is much lower than either of the two original frequencies, the resulting difference mean Doppler frequency will not be aliased.

3 Claims, 3 Drawing Figures

MULTIPLE DEMODULATION FREQUENCY DOPPLER

BACKGROUND OF THE INVENTION

The present invention relates to medical ultrasound diagnostic equipment. In particular it relates to Doppler blood velocity meters.

In the measurement of blood velocity using pulsed ultrasound Doppler equipment, there is a recognized problem in measuring the velocity of blood in deep lying vessels. The problem results from the fact that the pulse repetition frequency (hereinafter called "PRF") is determined, in part, by the depth within the body of the blood whose velocity is being measured. The PRF is typically selected such that a pulse can be transmitted from the transducer and reflected from blood flowing within the vessel with the return pulse being received prior to the transmission of the next succeeding pulse.

As used herein the term "sample volume" means the region of interest of blood flow velocity. The terms "sample volume" and "PRF" are well known and understood in the art, and it is also well known that the maximum PRF which can be used without introducing depth ambiguities is equal to the speed of sound in the medium divided by twice the depth of the sample volume.

A well recognized phenomenon, called "aliasing", wherein the blood flow appears to have a different velocity or direction than it actually has, occurs when blood flow exceeds a maximum velocity for a given ultrasound transmitted frequency. Aliasing results from the fact that the Doppler shift frequency is equal to twice the ultrasound transmitted frequency times the velocity of the moving blood divided by the velocity of sound in the body. When the Doppler frequency is more than one half the PRF, aliasing occurs. In other words, aliasing occurs when the maximum blood flow velocity is greater than or equal to the square of the speed of sound in the human body divided by eight times the ultrasound transmitted frequency times the sample volume depth. Accordingly, the maximum blood flow velocity which can be measured without exhibiting aliasing is inversely proportional to the sample volume depth in the body for a given ultrasound transmitted frequency.

While one approach to increasing the maximum velocity which can be measured without aliasing is to reduce the frequency of the ultrasound transmitted energy, if the frequency decreases below about 2 MHz, the scattering phenomenon, which is required for observing the return Doppler signals, is degraded. In addition, a reduction in the ultrasound transmitted frequency also reduces the resolution of the sample volume. Accordingly, the approach of decreasing the frequency of the ultrasound transmitted frequency can be helpful to about 2 MHz. Thereafter, decreasing the ultrasound transmitted frequency has not been found to be a desirable approach to use for eliminating the aliasing effect. Accordingly, a new approach to providing an unaliased signal would be desirable.

During normal operation of a pulsed Doppler system, a new burst is not transmitted until the return from the location of interest, i.e. the sample volume, is received. If the velocity of sound in body tissue is c, then the time of flight, T, from the transducer to the sample volume depth, d, and back is:

$$T = 2d/c$$

Thus, the highest PRF that is normally used is:

$$PRF_{max} = c/2d$$

The detected Doppler shifted frequency, $f_d$, of a target moving with velocity, v, detected with carrier frequency, $f_0$, is given by:

$$f_d = 2f_0 v/c$$

As $PRF/2$ is the highest frequency that can be measured without aliasing, $$f_d = PRF/2 = 2f_0 U_{max}/c$$

Accordingly, the highest velocity, $U_{max}$, which can be unambiguously detected is:

$$U_{max} = PRF^* c/4f_0 = (c^2)/(8f_0 d)$$

Heretofore, to prevent the problem of aliasing, either continuous wave Doppler was used, and all range resolution was lost, or, alternatively, the transmitted frequency was decreased. As noted above, decreasing the transmitted frequency only works down to a frequency of about 2 MHz due to decreased scattering. Increasing the PRF over $PRF_{max}$ introduces range ambiguities, and tracking the mean frequency as a function of time requires knowledge that the signal is not aliased at some point in time as a reference and the knowledge that it does not change too rapidly. (See "Resolution of Frequency Aliases in Ultrasound Pulsed Doppler Velocimeters", Craig Hartley, *IEEE Trans. Sonics and Ultrasonics*, Vol. SU-28, 1981, pp 69–75.). All of the foregoing approaches sacrifice some significant aspect of pulsed Dopplers, such as range resolution, or, alternatively, they require that some assumptions be made which may not be valid.

SUMMARY OF THE INVENTION

In accordance with the present invention, a broadband signal is transmitted. The Doppler shifted return is then detected at two different frequencies contained in the received wideband signal. If the mean frequency of each of the two signals is detected and the two are subtracted, the resulting frequency will be that which would have been produced by a system operating at the difference frequency. Thus, for reference local oscillators which operate at frequencies $f_1$ and $f_2$, respectively, the detected Doppler shifted return frequencies produced would be:

$$f_{d1} = 2vf_1/c,$$

and $$f_{d2} = 2vf_2/c$$

subtracting $f_{d2}$ from $f_{d1}$ gives:

$$f_d = f_{d1} - f_{d2} = 2v(f_2 - f_1)/c = 2v\Delta f_0/c$$

Thus, the detected Doppler frequency shift, $f_d$, is that which would have been produced by a Doppler system transmitting and demodulating at the difference frequency $\Delta f_0$ (equal to $f_2 - f_1$). Since $\Delta f_0$ can be made much smaller than $f_1$ or $f_2$, $f_d$ will be proportionally smaller than $f_{d1}$ or $f_{d2}$. Accordingly, the highest velocity that can be unambiguously detected is:

$$v_{max}=c^2/(8\Delta f_0 d)$$

If the frequencies are represented by binary numbers and binary arithmetic is used to perform the mean calculation in two's complement, so that $(127/128)*(+PRF/2)$ is represented by 01111111 (within 1/128 for 8 bit resolution), and $-PRF/2$ is represented as 10,000,000, the calculation is very simple. The difference frequency is calculated by simply subtracting the two binary numbers using modulus arithmetic, and the resulting binary number represents the mean frequency as a fraction of PRF/2.

DETAILED DESCRIPTION OF THE PREFERRED EMBODIMENT

Figure 1:
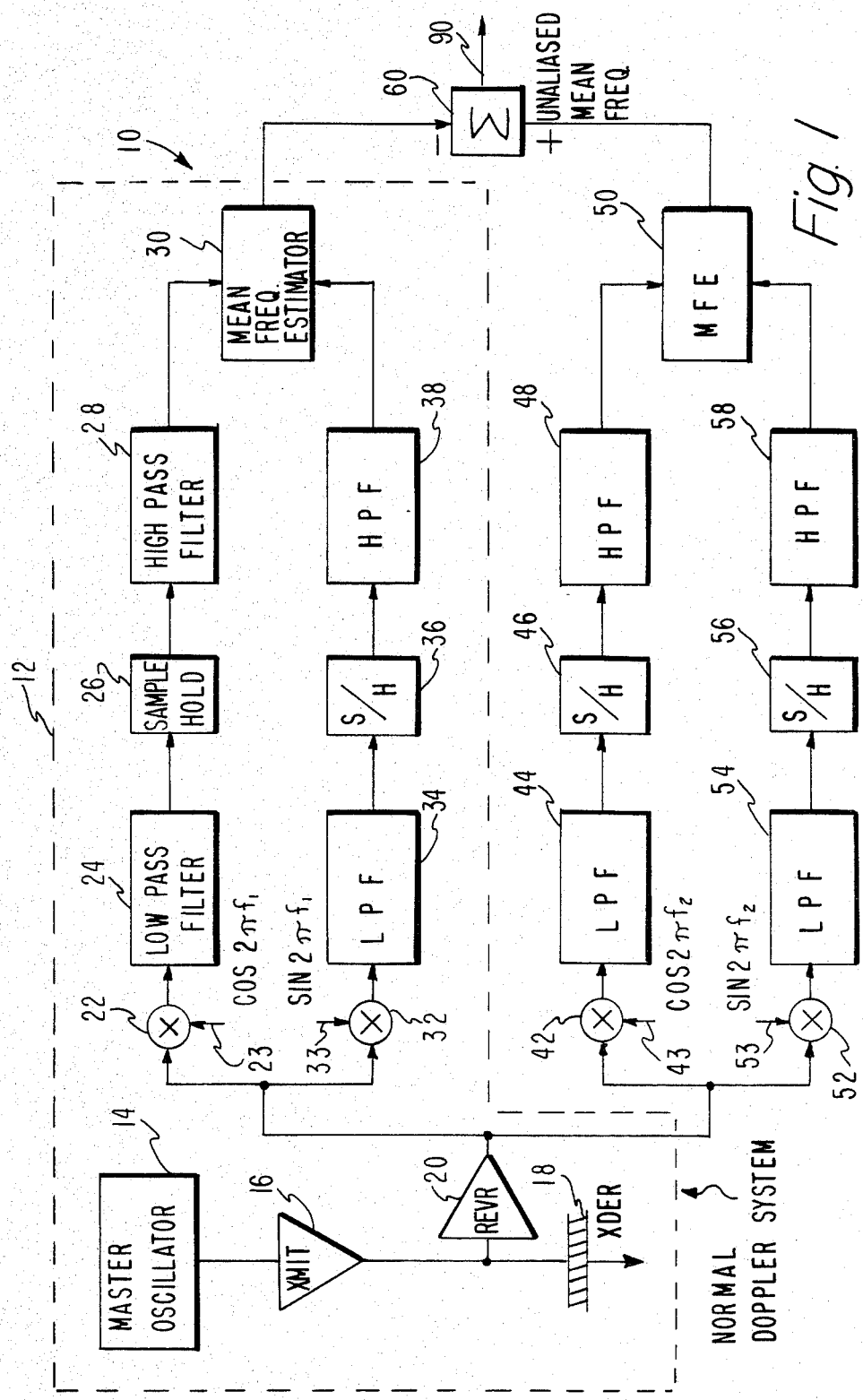
FIG. 1 is a block diagram of the present invention.

Referring now to FIG. 1, the device 10 of the present invention is shown. The invention includes a standard Doppler system 12 (shown within dashed lines). The standard Doppler system 12 includes a master oscillator 14 and a transmitter 16 which transmits signals through a transducer 18. Signals received from the transducer 18 are passed through a receiver amplifier 20 and through a first multiplier 22 which multiplies the received signal by COS $2\pi f_1$. The signal resulting from that multiplication goes through a low pass filter 24, a sample and hold circuit 26, and a high pass filter 28 into a mean frequency estimator 30. Similarly, the received signals from receiver 20 are passed through a multiplier 32 which multiplies them by SIN $2\pi f_1$ and the resulting signal is then sent through a low pass filter 34, a sample and hold circuit 36, and a high pass filter 38 into the mean frequency estimator 30.

In accordance with the present invention, the signals from the receiver 20 are also passed through a multiplier 42 where they are multiplied by COS $2\pi f_2$. Those signals are then sent through a low pass filter 44, a sample and hold circuit 46, and a high pass filter 48 into a mean frequency estimator 50. Similarly, received signals from receiver 20 are multiplied in multiplier 52 by SIN $2\pi f_2$ and sent into a low pass filter 54, a sample and hold circuit 56, and a high pass filter 58 into a mean frequency estimator 50. The outputs of the mean frequency estimators 30, 50 are sent into a subtractor 60 to obtain the unaliased mean frequency on output line 90.

Figure 2:
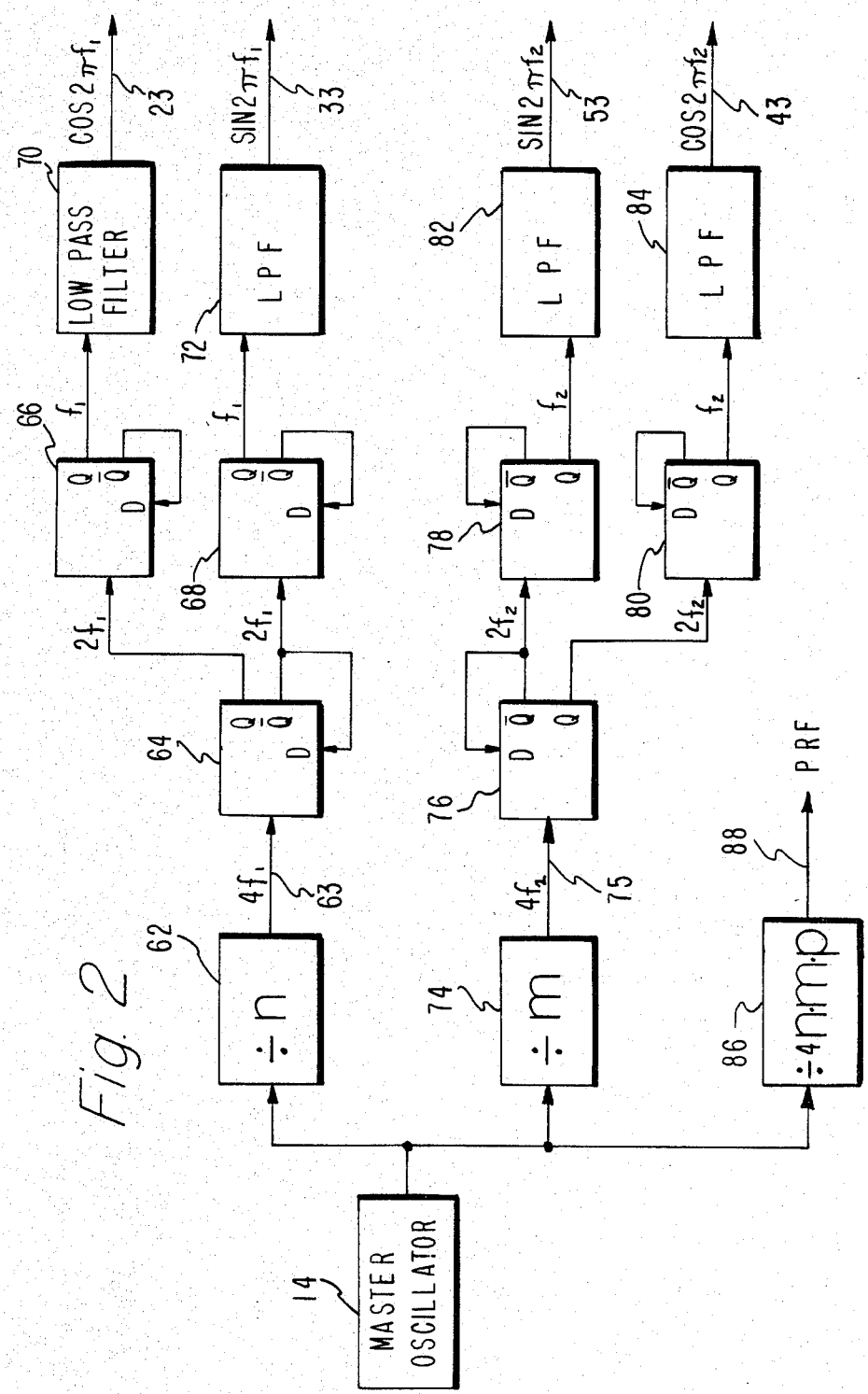
FIG. 2 is a block diagram showing the manner of generating the sinusoidal wave used in FIG. 1.

Referring now to FIG. 2, the method of generating the sinusoidal waves corresponding to COS $2\pi f_1$, SIN $2\pi f_1$, SIN $2\pi f_2$, and COS $2\pi f_2$ on lines 23, 33, 53, and 43, respectively, are shown. In particular, outputs from the master oscillator 14, which is made to oscillate at a frequency of 4 nmp$\times$PRF, where n,m and p are integers, are sent into a divide-by-n circuit 62 to obtain an output frequency corresponding to $4f_1$ on a line 63. Similarly, outputs from the master oscillator 14 are sent through a divide-by-m circuit 74 to obtain a signal corresponding to $4f_2$ on line 75, and into a divide-by-4 nmp circuit 86 to obtain a signal on line 88 which corresponds to PRF. The signal on line 63, corresponding to $4f_1$ is sent through a series of flip flops 64, 66, 68 which are set up as divide-by-2 circuits in order to reduce their frequency down to $f_1$ for input into low pass filters 70, 72. It should be noted that since the signal going into low pass filter 70 comes from the Q output of flip flop 64 whereas the input signal into the low pass filter 72 comes from the NOT Q output of the flip flop 64, they are out of phase with respect to one another. Accordingly, their outputs, on lines 23 and 33, respectively, correspond to COS $2\pi f_1$ and SIN $2\pi f_1$. Similarly, the outputs of low pass filters 82 and 84 correspond to SIN $2\pi f_2$ and COS $2\pi f_2$ on lines 53, 43.

Figure 3:
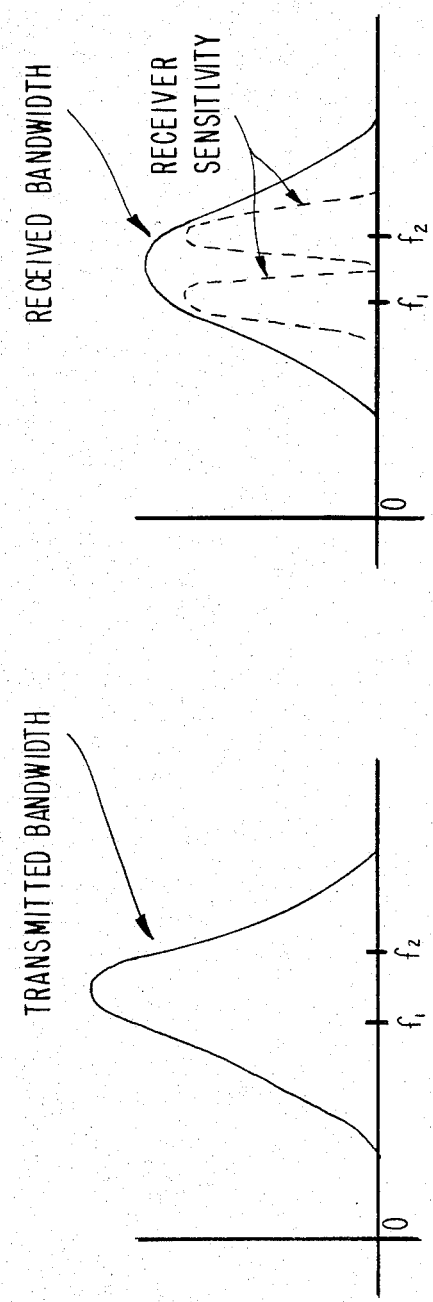
FIG. 3 is a frequency diagram showing the signals received by the present invention.

With reference to FIG. 3, the bandwidth of the signal transmitted is shown to include an area around the frequencies $f_1$ and $f_2$. Accordingly, the detected Doppler frequency shift $f_d$ on line 90 (See FIG. 1) is what would have been produced by a Doppler system operating at the frequency difference $\Delta f_0$ (equal to $f_2-f_1$).

As noted above, since $\Delta f_0$ can be much smaller than $f_1$ or $f_2$, $f_d$ will be proportionally smaller than $f_{d1}$ or $f_{d2}$. Accordingly, using the present invention, blood flow having a velocity of $v_{max}=c^2/(8\Delta f_0 d)$ can be detected.

I claim:

1. A multiple demodulation frequency Doppler detector for measuring the velocity of blood flowing in a patient's circulatory system comprising:
   (a) a first Doppler system including a master oscillator operating at a master oscillator frequency, a transmitter, a transducer, and a receiver, and means for generating a first sine wave and a first cosine wave having a first frequency which is said master oscillator frequency divided by a first integer;
   (b) a second Doppler system using said master oscillator, said transmitter, said transducer, and said receiver, and means for generating a second sine wave and a second cosine wave having a second frequency, different from said first frequency, said second frequency being said master oscillator frequency divided by a second integer different from said first integer;
   (c) said first Doppler system further includes means for detecting the mean Doppler frequency of said first Doppler system using said first sine wave and said first cosine wave;
   (d) said second Doppler system further includes means for detecting the mean Doppler frequency of said second Doppler system using said second sine wave and said second cosing wave; and
   (e) means for detecting the difference between said mean Doppler frequency of said first and second Doppler signals, whereby said difference will be the unaliased mean Doppler frequency.

2. The multiple demodulation frequency Doppler detector of claim 1 wherein said means for generating a first sine wave and a first cosine wave having a first frequency which is said master oscillator frequency divided by a first integer comprises:
   (a) a divide-by-n circuit, where n is an integer;
   (b) at least one flip flop having complementary outputs; and
   (c) low pass filter means associated with the complementary outputs of said flip flop.

3. The multiple demodulation frequency Doppler detector of claim 2 wherein said means for generating a second sine wave and a second cosine wave having a second frequency which is said master oscillator frequency divided by a second integer comprises:
   (a) a divide-by-m circuit, where m is an integer;
   (b) at least one flip flop having complementary outputs; and
   (c) low pass filter means associated with the complementary outputs of said flip flop.

* * * * *